United States Patent
Humayun et al.

(10) Patent No.: US 8,080,593 B2
(45) Date of Patent: Dec. 20, 2011

(54) REVERSIBLE THERMORESPONSIVE ADHESIVES FOR IMPLANTS

(75) Inventors: Mark Humayun, Glandale, CA (US); Buddy R. Ratner, Seattle, WA (US); James Weiland, Valencia, CA (US); Murat Tunc, Ankara (TR); Xuanhong Cheng, Bethlehem, PA (US)

(73) Assignee: University of Southern California, Los Angeles, CA (US)

( * ) Notice: Subject to any disclaimer, the term of this patent is extended or adjusted under 35 U.S.C. 154(b) by 665 days.

(21) Appl. No.: 11/947,770

(22) Filed: Nov. 29, 2007

(65) Prior Publication Data

US 2008/0140192 A1 Jun. 12, 2008

Related U.S. Application Data

(60) Provisional application No. 60/867,668, filed on Nov. 29, 2006.

(51) Int. Cl.
*C08G 61/02* (2006.01)
*A61B 19/00* (2006.01)
*A61B 17/08* (2006.01)
*A61B 17/04* (2006.01)
*A61L 17/00* (2006.01)
*A61F 2/16* (2006.01)
*A61F 2/18* (2006.01)

(52) U.S. Cl. ........ 523/111; 128/849; 606/151; 606/213; 606/215; 606/231; 623/6.63; 623/10

(58) Field of Classification Search ............... 523/111
See application file for complete search history.

(56) References Cited

U.S. PATENT DOCUMENTS

| | | | |
|---|---|---|---|
| 6,254,634 B1 * | 7/2001 | Anderson et al. | 623/1.42 |
| 6,270,872 B1 * | 8/2001 | Cline et al. | 428/40.1 |
| 6,323,278 B2 * | 11/2001 | Rhee et al. | 525/54.1 |
| 2003/0094237 A1 * | 5/2003 | Ogle et al. | 156/330 |
| 2004/0053334 A1 * | 3/2004 | Ratner et al. | 435/7.1 |
| 2004/0151691 A1 * | 8/2004 | Oxman et al. | 424/78.38 |
| 2005/0069589 A1 * | 3/2005 | Lowinger et al. | 424/488 |
| 2005/0080484 A1 * | 4/2005 | Marmo et al. | 623/5.14 |
| 2005/0118230 A1 * | 6/2005 | Hill et al. | 424/426 |
| 2005/0245966 A1 * | 11/2005 | Hammerslag et al. | 606/214 |
| 2006/0240552 A1 * | 10/2006 | Yamato et al. | 435/368 |

FOREIGN PATENT DOCUMENTS

WO  WO 2004070023 A1 * 8/2004

OTHER PUBLICATIONS

Matsuda, T., Poly(N-isopropylacrylamide)-grafted gelatin as a thermoresponsive cell-adhesive, mold-releasable material for shape-engineering tissues, Journal of Biomaterials Science Polymer Edition, 2004, vol. 15, No. 7, p. 947-955.*

Bioadhesives For Intraocular Use (Retina 2000;20:469-477) by Eyal Margalit, MD, Ph.D., et al.

(Continued)

*Primary Examiner* — Mark Eashoo
*Assistant Examiner* — David Karst
(74) *Attorney, Agent, or Firm* — DLA Piper LLP (US)

(57) ABSTRACT

The present invention relates to thermoresponsive adhesives. The invention further relates to methods for the reversible attachment of retinal implants, other implants, and drug delivery devices.

31 Claims, 3 Drawing Sheets

OTHER PUBLICATIONS

The Use of Tissue Adhesive in Corneal Perforations (Ophthalmology—1983;90:610-615) by Jack L. Weiss, MD, et al.

Octyl 2-cyanoacrylate tissue adhesive in experimental scleral buckling (Acta Ophthalmol Scand 2001;79:506-508) by Benedetto Ricci, et al.

Plasma Polymerized N-Isopropylacrylamide: Synthesis and Characterization of a Smart Thermally Responsive Coating (Biomacromolecules 2001;2:32-36) by Y. Vickie Pan, et al.

Novel cell patterning using microheater-controlled thermoresponsive plasma films (J. Biomed Mater Res 2004;70A:159-168) by Xuanhong Cheng, et al.

Novel thermally reversible hydrogel as detachable cell culture substrate (J. Biomed Mater Res 1998;40-631-639) by Horst A. von Recum, et al.

* cited by examiner

REVERSIBLE THERMORESPONSIVE ADHESIVES FOR IMPLANTS

The present application claims the benefit of the filing date of U.S. Provisional Application No. 60/687,668 the disclosure of which is incorporated herein by reference in its entirety.

Support from NSF grants EEC 0317023 and EEC 9529161 is acknowledged.

FIELD OF THE INVENTION

The present invention relates to reversible thermoresponsive adhesives.

BACKGROUND OF THE INVENTION

Building reliable interfaces between biological and engineered systems is one of the great challenges in biomimetic applications and for drug delivery purposes. A safe and effective adhesive can be very useful to implant a biomimetic microelectronic device inside the eye. Several adhesives such as hydrogels, fibrin sealants, and photocurable glues have been tested in previous studies for this purpose.[1-3] These adhesives exhibit limitations such as inflammation, toxicity, insufficient adhesive strength, irreversibility and deformation of the ocular tissue.[1-6]

Polymeric systems that may modify adhesive properties in response to changes in the physical and chemical characteristics of the physiological medium are promising candidates to achieve reversible tissue adhesion. Several groups have explored the use of dynamic stimulus-responsive surface chemistries for cell patterning.[1,7-9] Thermo-active,[7] electrical-active,[8] and photo-active[1,9] chemistries have been defined for cellular adhesion. In general, all of these chemistries operate under the same principle. These substances can be switched from a state that prevents cellular attachment to a state that promotes it.

A reversible, thermoresponsive adhesive could have many applications in opthalmology such as in posterior segment surgery, implantation of biometric microelectronic devices, and ocular drug delivery. Likewise, other sites in the body could benefit from a reversible bioadhesive strategy for localized delivery, surgical repair, or the attachment of prosthetic devices.

The ideal adhesive for intraocular use should be nontoxic and biocompatible. Previous reports showed that hydrogels such as SS-PEG and styryl-polyethylene glycol (ST-PEG) were effective but short-lasting and SS-PEG was toxic to the retina.[1] N-isopropyl acrylamide (NIPAM) is toxic to neural tissue however, polymerized N-isopropyl acrylamide (pNIPAM) is not toxic to neural tissue and is commonly used in cell and tissue cultures for its reversible cell adhesion properties.[11,15,16] Previous reports showed that cells may be attached and detached from pNIPAM coated culture dishes without exhibiting any changes in morphology.[11,15] pNIPAM has also been used in retinal pigment epithelial (RPE) cell cultures to provide RPE sheets for transplantation. RPE cells also showed no signs of toxicity or changes in morphology.[15] Interestingly, pNIPAM has also been used to stop bleeding in experimental liver injuries and no toxicity has been reported.[17] In addition, previous studies show that pNIPAM has a lower critical solution temperature of 31° C. in an aqueous environment.[11-12] This may indicate that the reversible thermoresponsive adhesive or hydrogel (pNIPAM) exhibits decreased solubility or swelling in water as the temperature is increased, due to a phase transformation at the lower critical solution temperature.[11-12] Thus, pNIPAM may be switched from a state that promotes cellular attachment to a state that prevents cellular attachment, as the temperature of the surface is decreased.

More specifically, cell adhesion onto a pNIPAM substrate surface can be regarded as a two-step process, with the first step controlled by complex combinations of physiochemical interactions including hydrophobic, Coulombic, and van der Waals forces between the cell and the surface. This process is often called 'passive' according to this adsorption mechanism. The second step is considered 'active' because of the participation of cellular metabolic processes, including focal adhesion development as well as cytoskeletal reorganization. However, when the temperature is decreased below pNIPAM's lower critical solution temperature at 31° C. the polymer becomes readily hydrated and hydrophilic. Similarly, cellular activity-independent detachment is defined as 'passive' and cellular activity-dependent attachment as 'active'.

SUMMARY OF THE INVENTION

In one embodiment, the invention relates to thermoresponsive adhesive substances that reversibly attach a material to a biological tissue.

In another embodiment, the invention relates to thermoresponsive adhesive substances that attach a material to a biological tissue at a critical temperature and allows for the detachment of the material from the biological tissue at a temperature that is below the critical temperature.

In a closely related embodiment, the invention relates to a composition comprising thermoresponsive adhesive substances that reversibly attach a material to a biological tissue.

In a accordance with another embodiment, the invention relates to a composition comprising thermoresponsive adhesive substances that attach a material to a biological tissue at a critical temperature and allows for the detachment of the material from the biological tissue at a temperature that is below the critical temperature.

Within one aspect, the present invention relates to methods of using thermoresponsive adhesive substances to reversibly attach a material to a biological tissue.

Within another aspect, the present invention relates to methods of using thermoresponsive adhesive substances to attach a material to a biological tissue at a critical temperature and allows for the detachment of the material from the biological tissue at a temperature that is below the critical temperature.

Within a closely related aspect, the present invention relates to reversible thermoresponsive adhesive substances that attach a material to a biological tissue for implantation, drug delivery, surgical repair, or the attachment of prosthetic devices.

Within a further related aspect, the present invention relates to methods of using reversible thermoresponsive adhesive substances that attach a material to a biological tissue for implantation, drug delivery, surgical repair, or the attachment of prosthetic devices.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

DETAILED DESCRIPTION OF THE INVENTION

Figure 1:
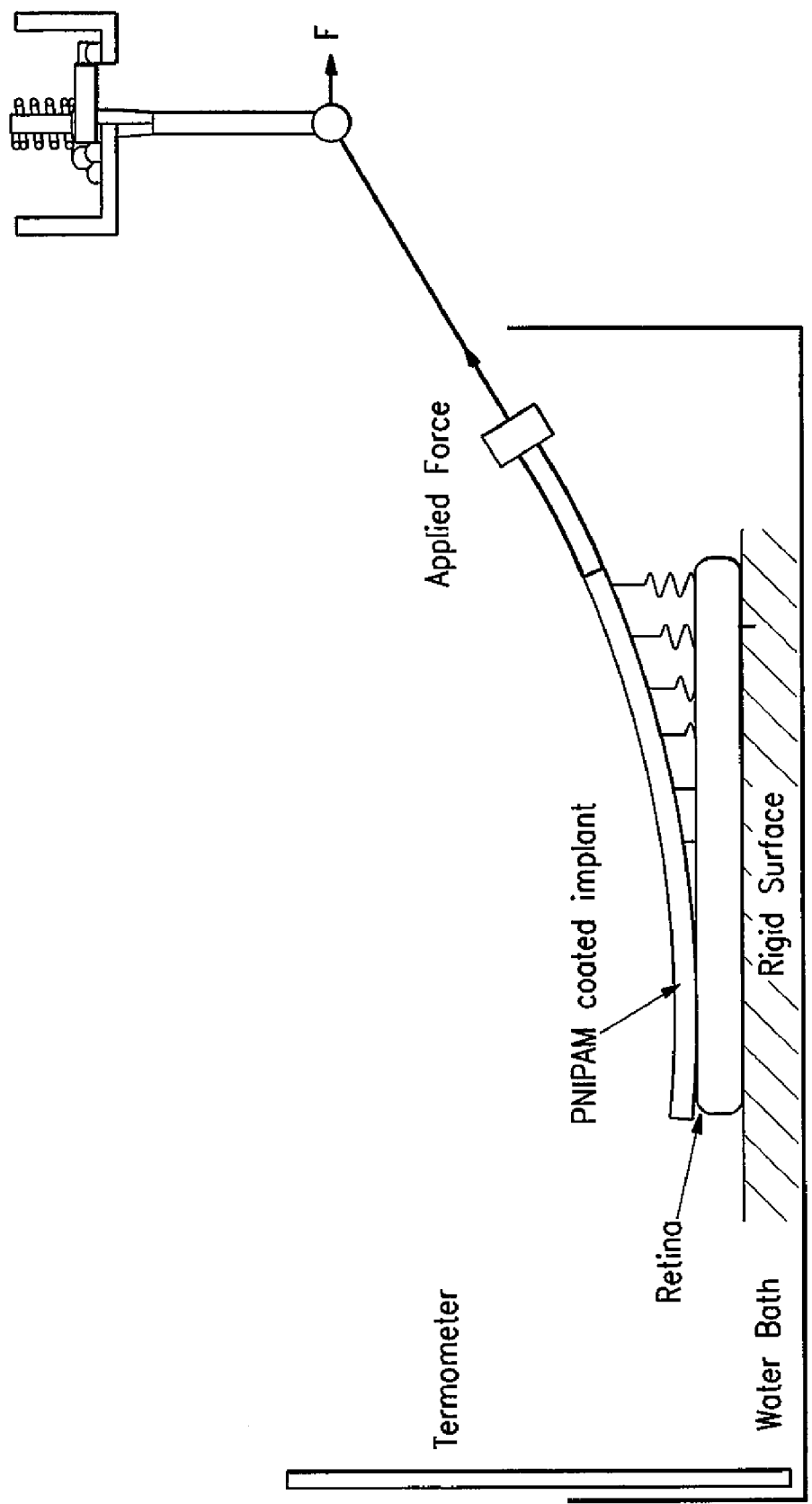
FIG. 1. Schematic diagram demonstrating the experimental design. (F=tractional force).

The present invention relates to compositions of thermoresponsive adhesives and methods of reversibly attaching materials to biological tissues.

As used herein the term "substance" refers to or describes a thermoresponsive adhesive that reversibly attaches a material to a biological tissue. Materials are coated with "substances." Examples of substances include but are not limited to alginate, cross linked alginate, hyaluraonic acid, collagen gel, fibrin glue, fibrin clot, agarose, chitin, chitosan, cellulose, polysaccharides, poly(oxy-alkylene), a copolymer of poly (ethylene oxide)-poly(propylene oxide), poly(vinyl alcohol), polyacrylate, plasma polymerized N-isopropyl acrylamide (ppNIPAM), polymerized N-isopropyl acrylamide (pNIPAM), N-isopropyl acrylamide (NIPAM), laiminin, solubilized basement membrane, or the like.

The term "material" as used herein refers to a material or implant that may be reversibly attached to a biological tissue. Examples of materials include but are not limited to poly (dimethyl siloxane) (PDMS), polyimide, or parylene C (poly (monochloro-p-xylylene)), or a combination thereof. A material may also be used for implantation, drug delivery, surgical repair, or the attachment of prosthetic devices. Examples may include but or not limited to a microelectronic retinal prosthesis, a biomimetic microelectronic device, a stent, a shunt, a stem cell, a punctum plug, an embryo, or any other materials that may be used for implantation, drug delivery, surgical repair, or the attachment of prosthetic devices.

In addition, a material may be secured using one or more agents including but not limited to tissue tacks, fasteners, staples, additional adhesives, sutures, or the like.

"Biological tissue" refers to any tissue that originates from a biological source. Examples of biological tissues include but are not limited brain, eye, mucous, buccal, tongue, tooth, gum, throat, esophageal, stomach, intestine, pancreas, liver, heart, artery, vein, muscle, knee cartilage, shoulder muscle, brain, testes, arterial wall, ocular tissue, retina, cornea, sclera, conjunctiva, palpebral mucosa, nasolacrimal duct, or the like.

"Thermoresponsive" refers to the ability of an adhesive to attach a material to a biological tissue at a critical temperature and allow the material to detach from the biological tissue at a temperature below the critical temperature.

"Critical temperature" refers to a temperature range wherein strong adhesion occurs between a material and biological tissue. For example, when using pNIPAM coated implants, strong adhesion between the implant and a retina is persistent at a critical temperature of about 32-38° C.

"Strong adhesion" is described as a strong stable force of at least 98 mN that when applied for 5 seconds to pull a material away from a biological tissue, the material does not detach from the tissue. Strong adhesion also refers to forces of 148 mN, 250 mN and forces up to 400 mN.

In one embodiment, three types of materials were used for retinal implantation: polyimide, parylene C (poly (monochloro-p-xylylene)) and poly(dimethyl siloxane) (PDMS). These are inert materials that are commonly used for insulation of the epiretinal electrode for epiretinal stimulation. Polyimide was prepared as 50 µm thick films, parylene as 20 µm thick films and PDMS was prepared at 200 µm in thickness at the biomedical engineering department of the University of Southern California.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLE 1

Posterior vitreous detachment (PVD) was created in porcine retina by soaking each porcine retina in 1.5 U (units) of plasmin for 4 days, while refrigerated at 4° C. pNIPAM-grafted parylene was attached to porcine retina at 37° C. in 15 trials and detached at 28±2° C. in all 15 trials.

To determine the adhesive strength, the retina was glued with cyanoacrylate to an aluminum cylinder and placed in a Bose ELF 3100 test instrument, and the parylene pNIPAM was adhered to the internal limiting membrane surface of the retina. The adhesive strength was measured using Dynamic Mechanical Analysis equipment. However, the retina was too delicate to quantify the adhesive strength of bioglues as the retina tears before adhesion fails. The adhesive strength was measured as either surface tension for controls (<10 mN i.e. plain parylene) or well above surface tension (50-400 mN) (data not shown).

EXAMPLE 2

Materials were coated with pNIPAM by plasma deposition as described by Pan, et al.[10] After NIPAM (97%) (Aldrich Milwaukee, Wis.) was polymerized, the exposed surface of the implant materials (polyimide, parylene and PDMS) were coated with pNIPAM. The pNIPAM-grafted surfaces were rinsed three times with cold deionized water to remove uncrosslinked molecules before use.

Enucleated pig eyes were transferred to the laboratory in cooled oxygenated 0.01 M phosphate-buffered saline (PBS, pH 7.4), and the cornea, lens, and vitreous were totally removed. Vertical relaxing incisions were performed through the eyecup from the periphery towards the optic disc, leaving the retina intact at the posterior pole. The retina was stabilized over a soft plastic sheet by pinning with four 25-Gauge needles, in order to keep the retina flat and facing upward over the scleral surface. This preparation was irrigated by phosphate buffered isotonic ringer lactate solution in a water bath.

The temperature was regulated using a thermostatic heater-controlled water bath to adjust the temperature of the retinal tissue. The tissue temperature was continuously checked during the experiment. pNIPAM coated materials, polyimide, parylene and PDMS were cut into 3×2 mm pieces. Five pieces were prepared for each material. A 7/0 suture was passed through one corner of the polyimide and parylene implants to apply tractional force (peel test) controlled by a strain gauge mechanism to measure the adhesive force (FIG. 1). As PDMS was too fragile to apply traction using the suture method, only vitreoretinal microforceps were used to check the retinal adhesion.

Five pre-prepared pNIPAM coated implants for each material and five controls without pNIPAM coating were used. Before retinal implantation, the water bath temperature was set at 22° C. The temperature of the water bath was gradually increased to 38° C. within 15 minutes. During the heating period, the implant was held over the retina with vitreoretinal forceps. The retinal adhesion between the pNIPAM coated materials and controls were checked continuously until body temperature (37° C.) was reached. Where adhesion was observed, the adhesive force was measured by a strain gauge (Somfy-Tec-France) attached to the suture. The temperature was then lowered back to 22° C. to test whether the adhesion is reversible.

Results

Figure 2:
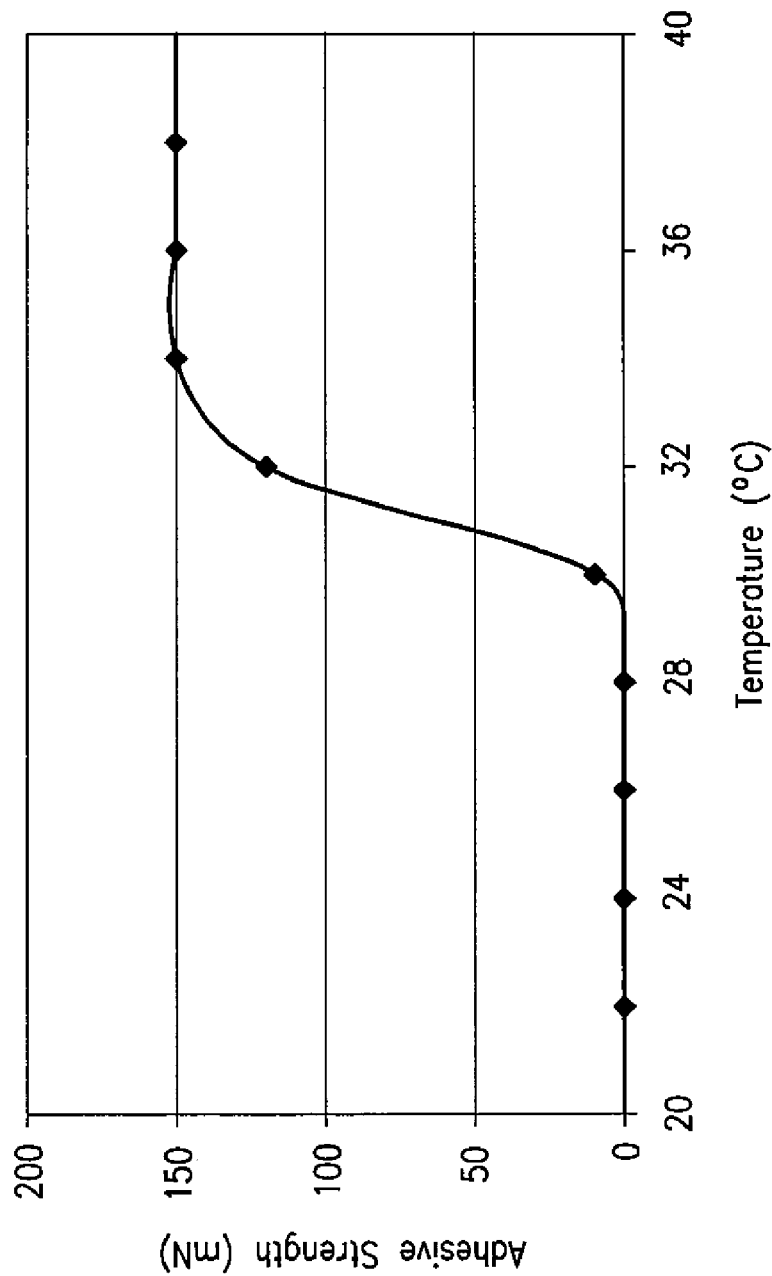
FIG. 2. Graph of temperature related changes as a function of adhesive strength of polymerized N-isopropyl acrylamide (pNIPAM) coated implants.
Figure 3:
FIG. 3. Photograph of the adhesion between the retina and a pNIPAM coated implant during a peel test.

There was no retinal adhesion at room temperature (22° C.) in any of the pNIPAM-coated materials (polyimide, parylene, and PDMS) and controls. Retinal adhesion developed in all pNIPAM coated test materials (polyimide, parylene, and PDMS) when the temperature reached 32° C. Strong adhesion developed within 60 seconds of reaching the critical temperature of 32° C. Adhesion was persistent between 32-38° C. (FIG. 2). A pull test by a suture attached to one corner of the polyimide and parylene implants was performed. Stable forces of 98 mN and 148 mN were applied for 5 seconds to pull the implants away from the retinal surfaces (FIG. 3). The adhesion was stable for both polyimide and parylene materials. The tractional force was increased up to 250 mN in two cases for each tested material and the retina tore or detached as the peeling force increased.

In PDMS, strong adhesion between 32-38° C. was observed and the implant was unable to be detached from the retinal surface with vitreoretinal forceps without detaching the retina from the scleral bed.

In the remaining three samples the temperature was lowered back to 22° C. by irrigation with cold BSS. When temperatures below 31° C. were reached, all attached implants began to detach from the retinal surface spontaneously without using tractional force and they detached from the retinal surface completely within two minutes when a temperature of 22° C. was reached. This demonstrated that the retinal adhesion of pNIPAM coated implants was reversible. There was no retinal adhesion in any of the controls without pNIPAM coating between 22° C. and 38° C.

Discussion

Parylene, polyimide and PDMS are inert materials that are commonly used for insulation of an epiretinal electrode for retinal stimulation. In these experiments pNIPAM coated implants showed strong adhesion with the retinal tissue above the critical or transition temperature. The adhesive strength of pNIPAM with the retinal tissue may be superior to cyanoacrylate[2], fibrin sealants[1] and CELL-TAK[1] (polyphenolic protein solution extracted from *Mytilus edulis* (marine mussel) and similar to hydrogels (succinimidyl succinate polyethylene glycol (SS-PEG) and succinimidyl propionate polyethylene glycol (SPA-PEG)).[1] Cell adhesion onto a material surface is controlled by complex combination of physicochemical interactions including hydrophobic, coulombic, and van der Waals forces between the cell membrane and the material surface and molecular interpenetrations of macromolecules. SPA-PEG hydrogels can make covalent links with the retina.[1] pNIPAM undergoes its phase transition by changes in hydrophobic interaction and the breaking of H-bonds. Also, spectroscopic data showed a change of the polymer backbone conformation.[13-14] Thus, while not wanting to be bound by the theory, the inventors believe that the adhesive force between retina and pNIPAM may be associated with the soluble, freely coiling chains that have slightly interpenetrated into the outer molecular structure of the retina and then undergone thermally-induced hydrophobic collapse (the change in backbone conformation) locking themselves within the outer zone of the retina.

Studies in porcine cadaver eyes showed that most of the measured force during retinal surgical manipulations was below 67 mN in magnitudes.[18] In these experiments, pNIPAM coated test materials (polyimide and parylene) were resistant to tractional forces of 98 mN and 148 mN. Additionally, the adhesive force between the retina and pNIPAM-coated PDMS was strong enough to resist the pulling force of a vitreoretinal forceps.

Studies in porcine cadaver eyes showed that most of the measured force during retinal surgical manipulations was below 67 mN in magnitudes.[18] In the present experiments, pNIPAM coated test materials (polyimide and parylene) were resistant to tractional forces of 98 mN and 148 mN. Additionally, the adhesive force between the retina and pNIPAM-coated PDMS was strong enough to resist the pulling force of a vitreoretinal forceps. In regards to an intraocular implant, the force from any device on the retina depends on the weight of the device in air and then adjusted for the buoyancy effects of the intraocular environment.

These experiments demonstrate that all pNIPAM-coated implants can be attached and detached from the retinal surface, simply by changing the temperature of the retinal tissue. This reversibility may be useful in the removal of an epiretinal stimulating electrode when necessary simply by using a cooled BSS infusion. In addition to its reversibility, pNIPAM coated implants may also provide better apposition of the electrode with the retinal surface for effective stimulation.[19]

The results demonstrate that reversible thermoresponsive adhesives may be useful in the implantation of nanotechnological systems within the eye. A person of ordinary skill in the art will realize that reversible thermoresponsive adhesives such as pNIPAM may have other applications in ophthalmic surgery and drug delivery.

Obviously, many modifications and variation of the invention as hereinbefore set forth can be made without departing from the spirit and scope thereof and therefore only such limitations should be imposed as are indicated by the appended claims.

All patent and literature references cited in the present specification are hereby incorporated by reference in their entirety.

REFERENCES

1. Margalit E, Fujii G Y, Lai J C, et al. Bioadhesives for intraocular use. Retina 2000; 20:469-477.
2. McCuen B W 2nd, Hida T, Sheta S M, et al. Experimental transvitreal cyanoacrylate retinopexy. Am J Opthalmol 1986; 15:199-207.
3. Peppas N A, Sahlin J J. Hydrogels as mucoadhesive and bioadhesive materials; a review. Biomaterials 1996; 17:1553-1561.
4. Weiss J L, Williams C, Lindstrom R L, Doughman D J. The use of tissue adhesive in corneal perforations. Opthalmology 1983; 90:610-615.
5. Liggett P E, Cano M, Robin J B, et al. Intravitreal biocompatability of mussel adhesive protein. A preliminary study. Retina 1990; 10:144-147.
6. Ricci B, Ricci F. Octyl 2-cyanoacrylate tissue adhesive in experimental scleral buckling. Acta Opthalmol Scand 2001; 79:506-508.
7. Yamato M, Kwon O H, Hirose M, et al. Novel patterned cell coculture utilizing thermally responsive grafted polymer surfaces. J Biomed Mater Res 2001; 55:137-140.
8. Yousaf M N, Houseman B T, Mrksich M. Using electroactive substrates to pattern the attachment of two different cell populations. Proc Natl Acad Sci USA 2001; 98:5992-5996.

9. Sanford M S, Charles P T, Commisso S M, et al. Photoactivatable cross-linked polyacrilamide for the siteselective immobilization of antigens and antibodies. Chem Mat 1998; 10:1510-1520.
10. Pan Y V, Wesley R A, Luginbuhl R, et al. Plasma polymerized N-isopropylacrylamide: Synthesis and characterization of a smart thermally responsive coating. Biomacromolecules 2001; 2:32-36.
11. Cheng X, Wang Y, Hanein Y, et al. Novel cell patterning using microheater-controlled thermoresponsive plasma films. J Biomed Mater Res 2004; 70A:159-168.
12. Pelton R. Temperature-sensitive aqueous microgels. Adv Colloid Interface Sci 2000; 85:1-33.
13. Badiger M, Wolf B A. Shear induced demixing and rheological behavior of aqueous solutions of poly(N-isopropyl acrylamide). Macromol Chem Phys 2003; 204:600-606.
14. Xiao X C, Chu L Y, Chen W M, et al. Positively Thermo-Sensitive Monodisperse Core-Shell MicrospheresAdv Funct Mater 2003; 13:847-852.
15. von Recum H A, Kim S W, Kikuchi A, et al. Novel thermally reversible hydrogel as detachable cell culture substrate. J Biomed Mater Res 1998; 40:631-639.
16. Okano T, Yamada N, Okuhara M, et al. Mechanism of cell detachment from temperature-modulated, hydrophilic-hydrophobic polymer surfaces. Biomaterials 1995; 16:297-303.
17. Nagaya M, Kubota S, Suziki N, et al. Evaluation of thermoreversible gelatin polymer for regeneration of focal liver injury. Eur Surg Res 2004; 36:95-103.
18. Jagtap A D, Riviere C N. Applied force during vitreoretinal microsurgery with handheld instruments. Proceedings of the 26th Annual International Conference of the IEEE EMBS, 2004: 2771-2773.
19. Heiduschka P, Thanos S. Implantable bioelectric interfaces for lost nerve functions. Prog Neurobiol 1998; 55:433-461.

What is claimed is:

1. A method of reversibly attaching a material to a biological tissue, comprising:
   providing a material having an area of a surface coated with a substance that becomes adherent at temperatures above 32° C.;
   contacting said substance with said biological tissue, and allowing the temperature of said substance to rise above 32° C.,
   wherein said substance will attach said material with said biological tissue once the temperature rises above 32° C. and said material will detach from said biological tissue when the temperature is allowed to reach below 32° C.,
   wherein an adhesive force between said substance and said tissue is greater than the weight of said material when attached to the biological tissue,
   wherein the temperature is raised by applying liquid with a temperature greater than 32° C.
2. The method of claim 1, wherein said substance is polymeric.
3. The method of claim 1, wherein said substance is applied to said material using a plasma deposition process.
4. The method of claim 1, wherein said substance is polymerized N-isopropyl acrylamide.
5. The method of claim 1, wherein said substance is plasma polymerized N-isopropyl acrylamide (ppNIPAM).
6. The method of claim 1, wherein said substance further comprises a component selected from the group consisting of alginate, cross linked alginate, hyaluraonic acid, collagen gel, fibrin glue, fibrin clot, agarose, chitin, chitosan, cellulose, polysaccharides, poly(oxy-alkylene), a copolymer of poly (ethylene oxide)-poly(propylene oxide), poly(vinyl alcohol), polyacrylate, plasma polymerized N-isopropyl acryl amide, polymerized N-isopropyl acrylamide, laiminin, solubilized basement membrane, and a combination thereof.
7. The method of claim 1, further comprising one or more agents to secure said material selected from the group consisting of tissue tacks, fasteners, staples, additional adhesives, and sutures.
8. The method of claim 1, wherein said material comprises poly(dimethyl siloxane), Polyimide, or parylene C (poly(monochloro-p-xylylene)), or a combination thereof.
9. The method of claim 1, wherein said biological tissue is ocular tissue.
10. The method of claim 1, wherein said biologic tissue is selected from the group consisting of cornea, sclera, conjunctiva and palpebral mucosa.
11. The method of claim 1, wherein said biologic tissue is retina.
12. The method of claim 1, wherein said material is a microelectronic retinal prosthesis.
13. The method of claim 12, further comprises one or more agents to secure said microelectronic retinal prosthesis, wherein said agents are selected from the group consisting of tissue tacks, fasteners, staples, additional adhesives, and sutures.
14. The method of claim 1, wherein said material is a biomimetic microelectronic device.
15. The method of claim 1, further comprising a means of repairing a ppNIPAM coated punctum plug for temporary occlusion of the nasolacrimal duct for dry eye.
16. The method of claim 1, further comprising a means of repairing an intraocular lens with ppNIPAM coated haptics inside the eye.
17. The method of claim 1, wherein said substance is polymerized N-isopropyl acrylamide, said material is parylene C (poly(monochloro-p-xylylene)), and said biological tissue is ocular tissue.
18. A method of reversibly attaching a material to a biological tissue, comprising:
   providing a material that is coated with a substance that becomes adherent at temperatures above 32° C.;
   contacting said substance with said material; and
   allowing the temperature of said substance to rise above 32° C., wherein said material attaches to said biological tissue once the temperature rises above 32° C.,
   wherein an adhesive force between said substance and said biological tissue is greater than the weight of said device when attached to the biological tissue,
   wherein the temperature is raised by applying liquid with a temperature greater than 32° C.
19. The method of claim 18, wherein said substance is polymerized N-isopropyl acrylamide.
20. The method of claim 18, wherein said substance is N-isopropyl acrylamide, polymerized N-isopropyl acrylamide, or plasma polymerized N-isopropyl acryl amide, or a combination thereof.
21. The method of claim 18, wherein said material is biodegradable.
22. The method of claim 18, wherein said material comprises fibrin.
23. The method of claim 18, wherein when said material is attached to said biological tissue, bleeding is controlled.
24. The method of claim 18, wherein said material is a glaucoma shunt.
25. The method of claim 18, wherein when said material is attached to said biological tissue, a barrier is formed to by separating apposing tissue surfaces.

26. The method of claim 18, wherein the material comprises stem cells.

27. The method of claim 26 wherein said biological tissue is ocular tissue.

28. The method of claim 18, wherein said material comprises a local radiotherapy agent.

29. The method of claim 18, wherein said material is an episcleral or other ocular or periocular implant to deliver a chemotherapeutic-antineoplastic agent for treatment of intraocular tumors or other drugs.

30. The method of claim 18, wherein said substance is polymerized N-isopropyl acrylamide, said material is parylene C (poly(monochloro-p-xylylene)), and said biological tissue is ocular tissue.

31. A method of reversibly attaching a material to a biological tissue, comprising:
 providing a material that is coated with a substance that becomes adherent at temperatures above 32° C.;
 contacting said substance with said material; and
 allowing the temperature of said substance to rise above 32° C., wherein said material attaches to said biological tissue once the temperature rises above 32° C., wherein an adhesive force between said substance and said biological tissue is greater than the weight of said device when attached to the biological tissue, and
 collecting cell samples from an ocular surface with said material.

* * * * *